United States Patent
Khuri-Yakub et al.

(10) Patent No.: US 8,843,190 B2
(45) Date of Patent: Sep. 23, 2014

(54) MEDICAL SCREENING AND DIAGNOSTICS BASED ON AIR-COUPLED PHOTOACOUSTICS

(75) Inventors: Butrus T. Khuri-Yakub, Palo Alto, CA (US); Omer Oralkan, Morrisville, NC (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 13/554,985

(22) Filed: Jul. 20, 2012

(65) Prior Publication Data

US 2013/0023752 A1    Jan. 24, 2013

Related U.S. Application Data

(60) Provisional application No. 61/572,842, filed on Jul. 21, 2011.

(51) Int. Cl.
*A61B 5/05* (2006.01)
*A61B 5/00* (2006.01)

(52) U.S. Cl.
CPC .............. *A61B 5/0095* (2013.01); *A61B 5/0507* (2013.01)
USPC .............. 600/407; 600/463; 600/309; 604/66

(58) Field of Classification Search
None
See application file for complete search history.

(56) References Cited

U.S. PATENT DOCUMENTS

| | | | |
|---|---|---|---|
| 4,091,681 A * | 5/1978 | Hordvik | 73/574 |
| 6,041,020 A | 3/2000 | Caron et al. | |
| 6,216,540 B1 * | 4/2001 | Nelson et al. | 73/633 |
| 6,309,352 B1 | 10/2001 | Oraevsky et al. | |
| 6,662,040 B1 * | 12/2003 | Henrichs et al. | 600/431 |
| 6,833,554 B2 | 12/2004 | Wooh | |
| 7,322,972 B2 * | 1/2008 | Viator et al. | 606/9 |
| 7,665,364 B2 * | 2/2010 | Su et al. | 73/643 |
| 8,025,406 B2 | 9/2011 | Zhang et al. | |
| 8,426,933 B2 * | 4/2013 | Yacoubian | 257/416 |
| 2002/0035327 A1 * | 3/2002 | Kruger | 600/437 |
| 2006/0184042 A1 * | 8/2006 | Wang et al. | 600/476 |
| 2007/0220978 A1 * | 9/2007 | Su et al. | 73/632 |
| 2010/0033710 A1 * | 2/2010 | Yacoubian | 356/72 |
| 2010/0249570 A1 * | 9/2010 | Carson et al. | 600/407 |
| 2010/0268042 A1 * | 10/2010 | Wang et al. | 600/322 |
| 2012/0179029 A1 * | 7/2012 | Kircher et al. | 600/421 |
| 2012/0217399 A1 * | 8/2012 | Yacoubian | 250/338.1 |
| 2012/0323112 A1 * | 12/2012 | Jokerst et al. | 600/420 |
| 2012/0330157 A1 * | 12/2012 | Mandella et al. | 600/443 |
| 2013/0023752 A1 * | 1/2013 | Khuri-Yakub et al. | 600/407 |

OTHER PUBLICATIONS

Zhang et al., "In vivo imaging of subcutaneous structures using functional photoacoustic microscopy", 2007, pp. 797-804, Nature Protocols v2n4.

(Continued)

*Primary Examiner* — Nicholas Evoy
(74) *Attorney, Agent, or Firm* — Lumen Patent Firm

(57) ABSTRACT

Surface selective photoacoustic (PA) medical imaging is introduced. Surface selective PA imaging is responsive to surface features and does not image sub-surface features, in contrast to conventional PA imaging. The surface PA signal can be considerably larger than the bulk PA signal, for an air-coupled (or gas-coupled) acoustic transducer. Distinguishing these two signals based on time of arrival at the transducer can further distinguish the two signals. This approach provides numerous advantages. Non-contact imaging simplifies and expedites imaging, and can serve as a replacement for visual inspection by physicians. Applications include skin screening and endoscopy.

7 Claims, 4 Drawing Sheets

(56) References Cited

OTHER PUBLICATIONS

Kolkman et al., "Feasibility of noncontact piezoelectric detection of photoacoustic signals in tissue-mimicking phantoms", 2010, pp. 055011-1 to 055011-4, Journal of Biomedical Optics v15n5.

Zhang et al., "Functional photoacoustic microscopy for high-resolution and noninvasive in vivo imaging", 2006, pp. 848-851, Nature Biotechnology v24n7.

* cited by examiner

MEDICAL SCREENING AND DIAGNOSTICS BASED ON AIR-COUPLED PHOTOACOUSTICS

CROSS REFERENCE TO RELATED APPLICATIONS

This application claims the benefit of U.S. provisional patent application 61/572,842, filed on Jul. 21, 2011, entitled "Medical screening and diagnostics based on air-coupled photoacoustics", and hereby incorporated by reference in its entirety.

FIELD OF THE INVENTION

This invention relates to photoacoustic (PA) imaging for medical applications.

BACKGROUND

The generation of sound by light is known as the photoacoustic effect. Briefly, absorption of electromagnetic radiation in a sample leads to localized heating of the sample. The heated region of the sample will expand due to thermal expansion, and this expansion can launch acoustic waves in the sample. Imaging of the resulting acoustic waves is often referred to as photoacoustic imaging. PA imaging has been used for imaging sub-surface defects in materials for non-destructive evaluation.

Recently, PA imaging has been employed for biomedical applications. In these applications, typically a short laser pulse is transmitted into tissue. The introduced light energy is absorbed in a different manner by different parts of the tissue. The optical absorption depends on the wavelength of the light and the absorption properties of the medium. The regions with stronger absorption characteristics in a tissue generate stronger acoustic signals via the PA effect. By collecting these light-induced acoustic signals using an acoustic transducer, one can construct an image that is a representation of light absorption characteristics of the sample. One example of this approach is to image the sub-surface microvasculature in tissue by detecting blood oxygenation, which is usually a sign of angiogenesis indicating a cancerous lesion. In this example, the increased light absorption of the oxygenated blood at a certain wavelength is used to create a high-contrast sub-surface image.

Typically, such conventional PA imaging for biomedical application requires physical contact of the acoustic transducer to the patient, or the use of an impedance matching liquid or gel between the patient and the transducer. The reason for this is that if air (or any other gas) separates the patient from the transducer, there will be a large acoustic impedance mismatch at the patient-air interface, which will significantly and undesirably reduce the acoustic signal. This is explained in greater detail in connection with FIG. 1 below.

Some workers have accepted this loss due to acoustic impedance mismatching in order to realize various advantages of a non-contact configuration. For example, an article by Kolkman et al. (Feasibility study of non-contact piezoelectric detection of photoacoustic signals in tissue-mimicking phantoms, Journal of Biomedical Optics v15n5, Sep/Oct 2010, pp. 055011-1 to 055011-4) considers the imaging of a subsurface feature (artificial blood vessel in a phantom) where a 7.5 mm air gap is present between the phantom and the acoustic transducer. In this experiment, the optical illumination is provided to the side of the phantom.

However, there are aspects of PA imaging which do not appear to have been appreciated in the art. Accordingly, the considerations described below provide an advance in the art.

SUMMARY

In this work, surface selective PA imaging is introduced. As opposed to conventional PA imaging, which is responsive to sub-surface features, surface selective PA imaging is responsive to surface features and does not image sub-surface features. In general, both acoustic and electromagnetic radiation can penetrate to a significant depth in a patient, so the possibility of surface selective PA imaging is rather surprising. In other words, one would expect the bulk PA signal to dominate the surface PA signal. However, we have found, surprisingly, that the surface PA signal can be considerably larger than the bulk PA signal, for an air-coupled (or gas-coupled) acoustic transducer. Distinguishing these two signals based on time of arrival at the transducer can further distinguish the two signals.

The present approach of surface-specific PA imaging provides numerous advantages. Non-contact imaging simplifies and expedites imaging, and can serve as a replacement for visual inspection by physicians. Imaging of superficial targets, such as skin, are of considerable interest in practice. For example, basal cell carcinoma is the most common form of cancer in the United States, with more than 1,000,000 new cases presently expected per year. Presently, screening for skin cancer is performed by a physician who checks size, shape, color and texture of suspicious areas. For example, abnormal areas of skin tend to be more mechanically rigid than normal skin.

The present approach is especially suitable for such cases, because the PA image depends on both the optical and acoustic properties of the skin. Thus, surface-selective PA imaging can provide non-contact evaluation of skin texture (e.g., areas of abnormally rigid (or soft) skin), which is a capability that cannot be provided by any purely optical approach, such as conventional visual imaging. Such visual imaging also assumes a lesion is visible to attract the attention of the patient and then the doctor. The present approach has the potential for detecting lesions before they are visually distinguishable. Another application of the present approach is to endoscopy, where color, size, shape and texture of suspicious superficial features inside hollow organs (e.g., stomach, colon, esophagus, etc.) can be evaluated in a non-contact mode. A further application is for monitoring the healing of burns and skin transplants—non-contact evaluation is a particular advantage here.

DETAILED DESCRIPTION

Figure 1:
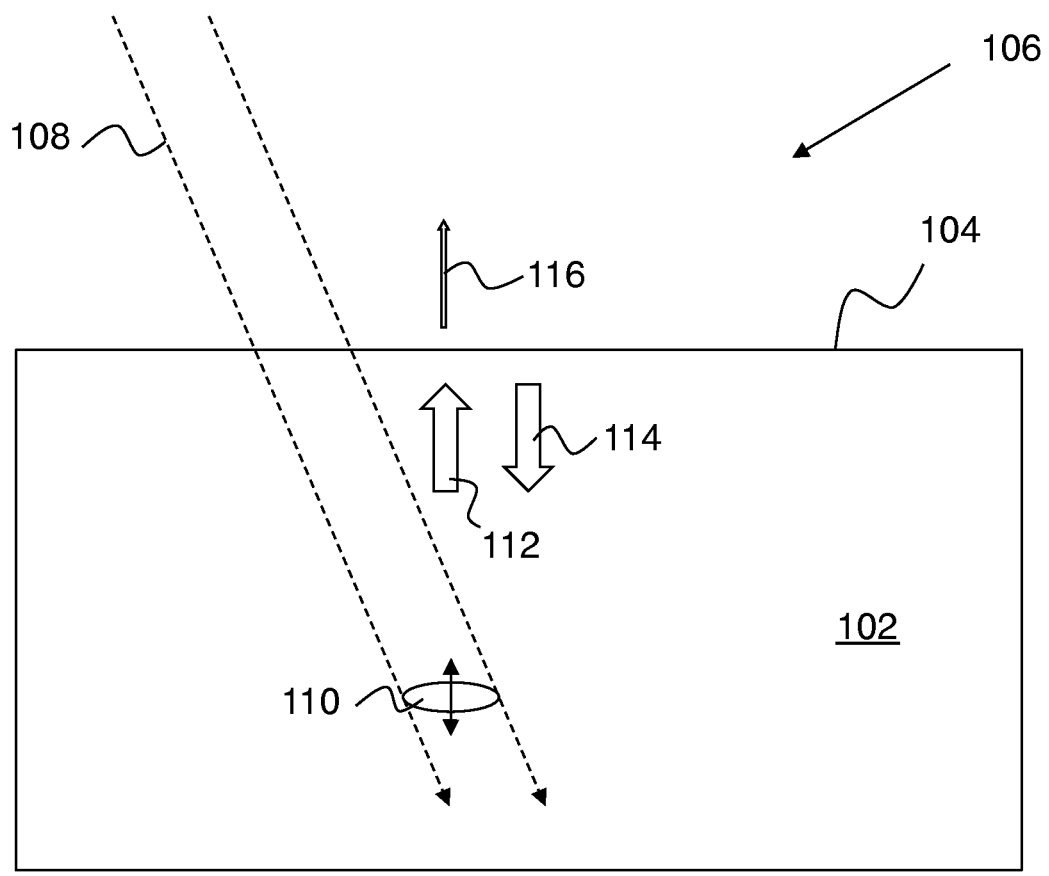
FIG. 1 shows the conventional bulk photoacoustic effect.

To better appreciate the present approach, it is helpful to review some features of the conventional PA effect, as shown on FIG. 1. Here a sample 102 is illuminated with a beam of electromagnetic radiation 108 (which is typically a pulsed beam). Within illuminated parts of sample 102, localized regions (e.g., 110) expand (when illuminated by a pulse) and contract (between pulses). This motion of region 110 (and similar regions, not shown for clarity) launches acoustic radiation 112 that propagates toward surface 104 of sample 102. The medium 106 above sample 102 is air (or any other gas). There is a large acoustic impedance mismatch between sample 102 and gas medium 106, so a large fraction of acoustic radiation 112 is reflected back into sample 102 as reflected acoustic radiation 114, and only a small fraction of acoustic radiation 112 is transmitted from sample 102 as transmitted acoustic radiation 116. For typical numbers (e.g., acoustic impedances for tissue and air of 1.5e6 $Nsm^{-3}$ and 400 $Nsm^{-3}$ respectively), the energy reflection coefficient is about 99.95%, so only about 0.05% of the available acoustic energy is able to leave sample 102 as transmitted radiation 116.

Figure 2:
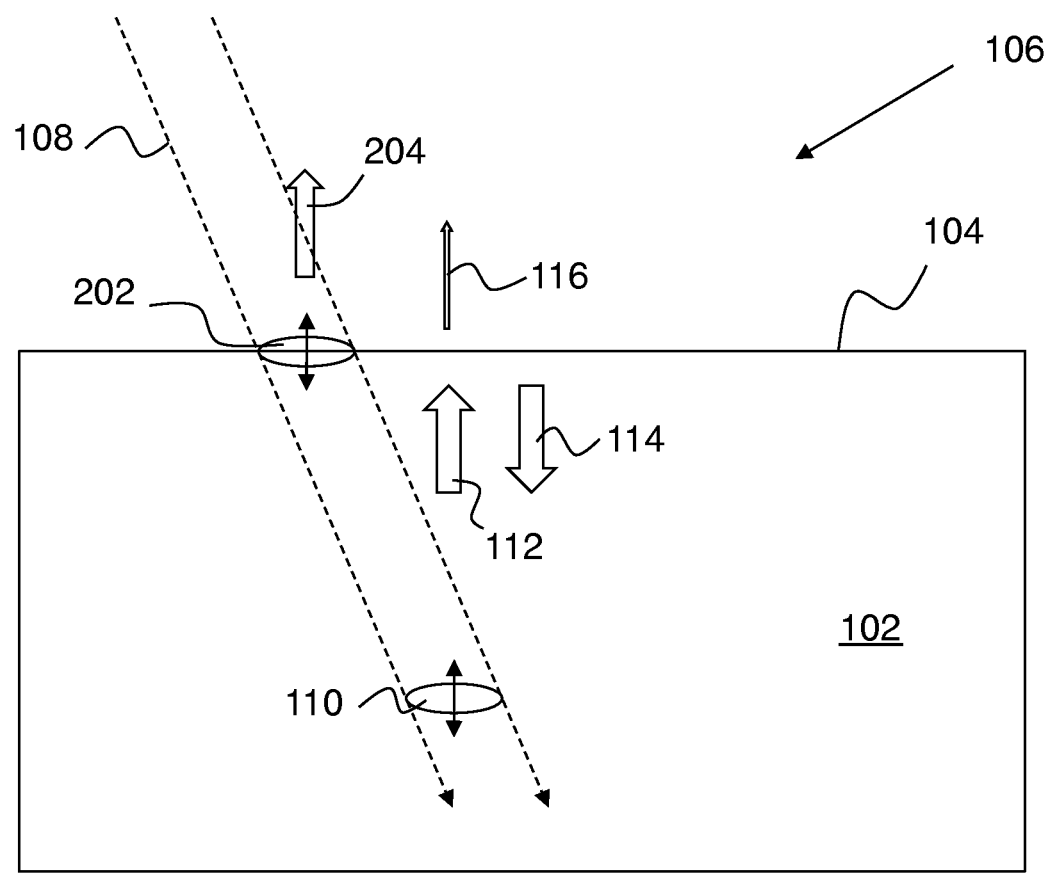
FIG. 2 shows the surface-specific photoacoustic effect.

FIG. 2 shows the surface-specific photoacoustic effect. Here a location 202 on surface 104 expands and contracts as a result of illumination by pulses in beam 108. Because location 202 is on surface 104, surface PA radiation 204 is emitted directly by the motion of region 202 into medium 106. As a result of this direct emission of acoustic radiation into gas medium 106, the large signal loss due to the acoustic impedance mismatch is avoided. For typical numbers relating to a tissue sample 102 and air as medium 106, rough order of magnitude estimated surface PA radiation 204 is about 1 Pa or more, while the estimated bulk PA radiation 116 is roughly 0.1 Pa. Thus, the surface PA signal can be substantially greater than the bulk PA signal in an air-coupled configuration.

In one embodiment, a method includes the following steps:
1) A superficial region of a patient is illuminated with electromagnetic radiation (e.g., optical, microwave, etc). For convenience, the term "photoacoustic effect" is taken to apply to acoustic excitation by electromagnetic radiation in any part of the electromagnetic spectrum. The superficial region of the patient has an exposed surface, and the beam of electromagnetic radiation makes a spot on this exposed surface. The beam can be focused or non-focused (e.g., "spot" includes flood illumination of part or all of the exposed surface as a limiting case).
2) At least one acoustic receiver is disposed to receive acoustic radiation from the beam spot on the exposed surface. The acoustic receiver(s) and the exposed surface are separated from each other by a gaseous medium (e.g., air). Practice of the invention does not depend critically on the composition of this gaseous medium.
3) The acoustic receiver(s) are responsive to surface PA radiation generated by EM absorption at the exposed surface.
4) The acoustic receiver(s) are less responsive to bulk PA radiation than to the surface PA radiation. The reduced amplitude of the bulk PA signal relative to the surface PA signal provides one way to distinguish the two signals. As indicated above, time of arrival information at the acoustic receiver(s) can also be used to further distinguish the surface PA signal from the bulk PA signal. For example, gas-coupled PA signals can be made surface-specific by looking at the leading edges of received acoustic pulses and discarding other parts of the pulses.

Numerous variations are possible. For example, functional contrast for superficial imaging can be provided (or enhanced) by one or more contrast agents. Such contrast agents can be endogenous or exogenous. Contrast agents can be applied topically, or can be introduced systemically (e.g., by injection). The superficial region of the patient can be skin (e.g., for skin screening applications). Alternatively, the superficial region of the patient can be a hollow organ (e.g., for non-contact evaluation of suspicious areas during endoscopy). Such non-contact evaluation can advantageously provide an image of optical and/or acoustic properties of the exposed surface. For example, abnormalities in skin elasticity can be evaluated without making physical contact to the skin.

Figure 3:
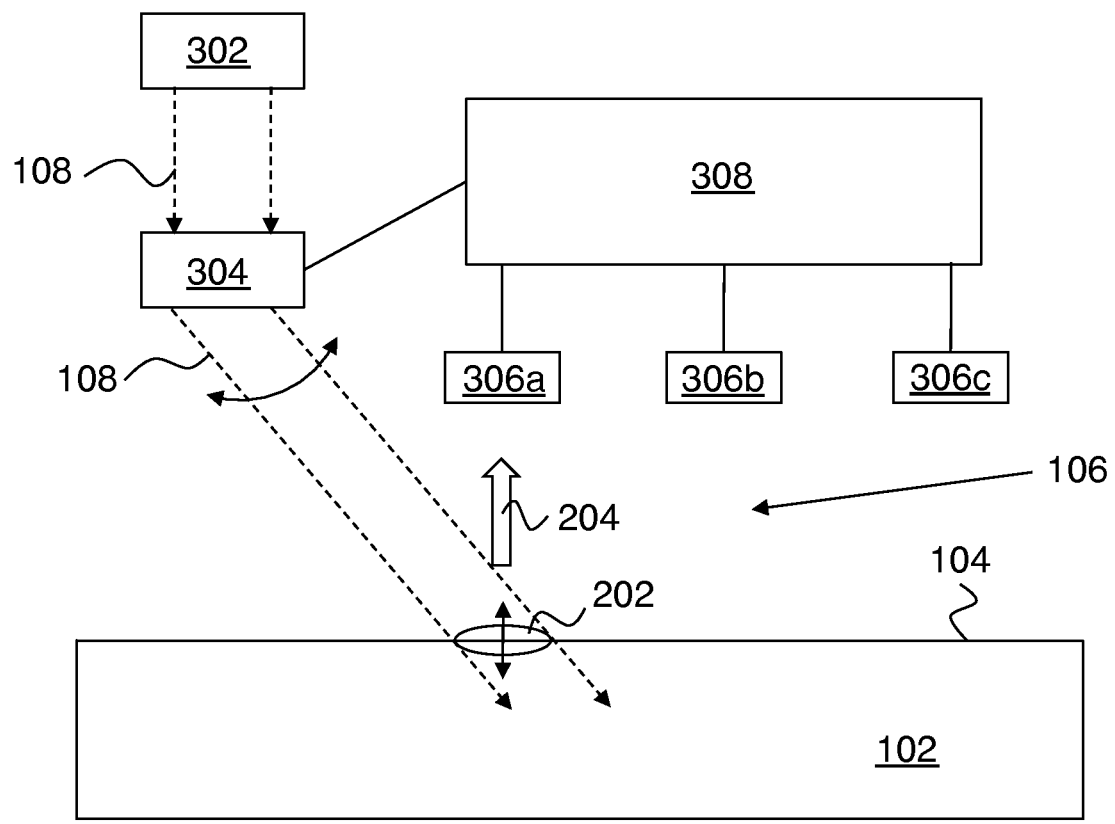
FIG. 3 shows an embodiment of the invention.

FIG. 3 shows an embodiment of the invention. In this example, a source 302 provides a beam of electromagnetic radiation 108. A scanner 304 is capable of moving beam 108 to various locations on exposed surface 104 of a superficial patient region 102. Surface PA radiation 204 is received by one or more acoustic receivers. In this example, an array of three acoustic receiver elements 306a, 306b and 306c is shown. A single detector can be employed, or detector arrays having any number or arrangement of detector elements can be employed. Multiple acoustic detectors can improve the signal to noise ratio and/or provide localization information. Any kind of acoustic receiver can be employed (e.g., piezoelectric sensors, electrostatic sensors, micro machined capacitive sensors, acoustic sensors based on laser interferometry etc).

A gaseous medium 106 separates the acoustic receivers 306a-c from exposed surface 104. Acoustic receivers 306a-c are responsive to surface PA radiation 204, and are less responsive to bulk PA radiation (not shown on FIG. 3). As indicated above, the amplitude difference and/or time difference between the surface PA and bulk PA signals can be used to provide this surface-selectivity.

A scanning configuration as shown on FIG. 3 is often preferred, but is not required. If scanning is not employed, the resulting system is a single-point system for non-contact monitoring.

Scanner 304 can scan the beam of EM radiation 108 over surface 104 under the control of a processor 308 that also receives the outputs from the acoustic detector(s). Thus, processor 308 can be configured to provide acoustic response vs. beam spot location, which effectively provides imaging where the beam spot provides the spatial resolution. This approach of using the EM beam to define the image points is in contrast to the more conventional approach of using flood EM illumination and using an acoustic detector array to provide spatial resolution for PA imaging. Surface selective PA imaging can be performed at one or several EM wavelengths. Use of several EM wavelengths can provide spectral information that may help to improve screening efficacy. Practice of the invention does not depend critically on how beam 108 is scanned. Suitable scanning approaches include moving mirrors and electronically controlled devices such as spatial light modulators. Scanning can be performed for the whole body, or for any superficial area, part or organ of the body.

The pulse repetition rate of source 302 sets the operating frequency of the system. Alternatively, source 302 can be a modulated continuous-wave source, and in this case, the modulation frequency of source 302 sets the operating frequency of the system. Preferably, this operating frequency is at the low end of the ultrasound frequency range (up to 1 MHz as the attenuation of sound in air is about 1.6 dB/cm and increases as the square of the frequency). Alternatively, the operating frequency can be in the audible frequency range (e.g., 20-20,000 Hz). Appropriate acoustic detectors can be used, depending on the frequency (e.g., ultrasound transducers for ultrasound frequencies, microphones for audible frequencies, etc.).

Apparatus as on FIG. 3 can be included in any kind of superficial medical imaging apparatus. Examples include skin screening apparatus and endoscopes.

Figure 4A:
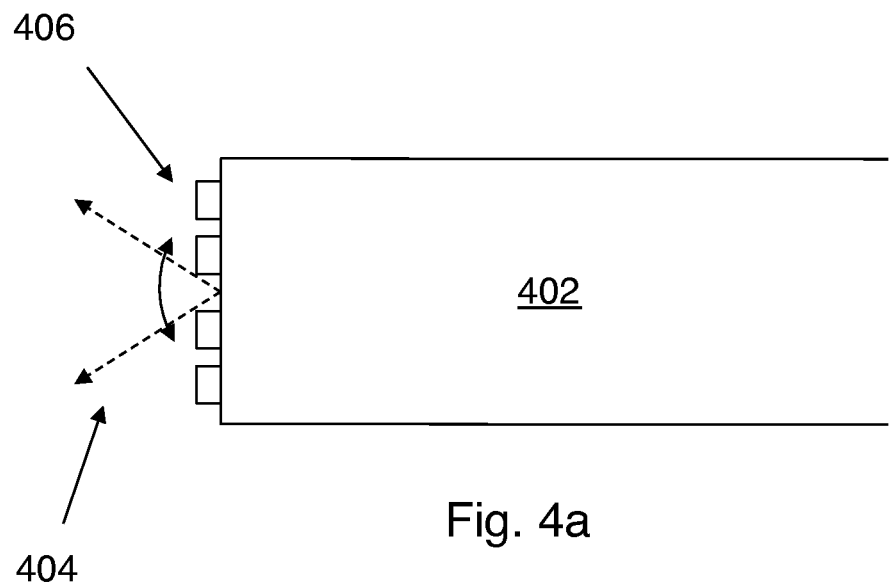
FIGS. 4a-b show further embodiments of the invention.
Figure 4B:
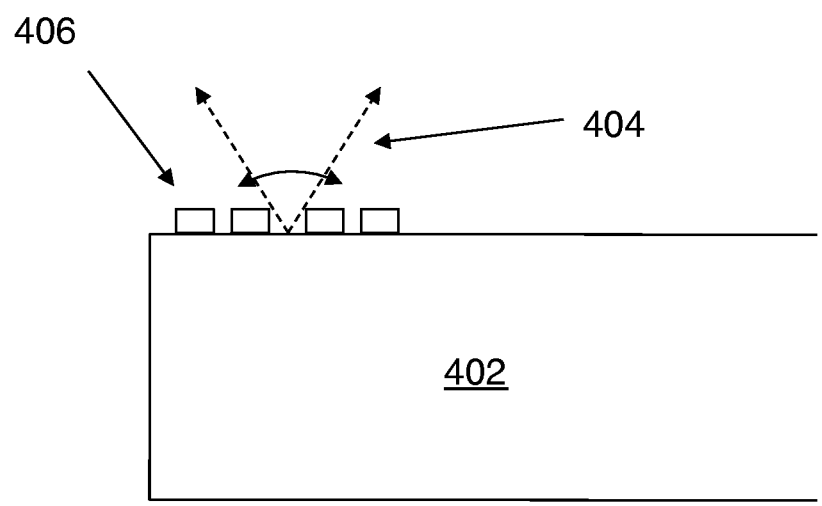

FIGS. 4a-b show further embodiments of the invention relating to endoscopes. FIGS. 4a and 4b show end-view and side-view endoscope imaging configurations, respectively. In these examples, endoscope tip 402 has a scannable EM beam 404 and acoustic receiver(s) 406 disposed on it. Other parts of the imaging apparatus, such as a processor, are not shown on FIGS. 4a-b, because they need not be at the endoscope tip and can be located elsewhere (e.g., in the endoscope control unit). In endoscopy, the endoscope is often separated from the exposed surface of a superficial patient region by a gaseous medium, thereby making the present approach applicable.

To demonstrate the feasibility of this approach we designed and conducted several proof-of-principle experiments. In these experiments we used a 40-kHz acoustic transducer that was commercially available for ultrasonic distance sensing applications (Parallax Inc., Rocklin, Calif., Model PING)))™). A pulsed laser beam with 532-nm wavelength, 0.9-mJ energy per pulse, and 7-ns pulse width was provided from a Q-switched Nd-YAG laser source (New Wave Research, Fremont, Calif., Model MiniLase-20) and was focused to a 4-mm spot. A target phantom was constructed by painting a 4-mm spot with black ink on a rubber-based tissue mimicking material (ATS Laboratories, Bridgeport, Conn.). The laser beam was aimed on the phantom. Using the acoustic transducer placed on the same side as the optical beam, we first performed a pulse-echo measurement to measure the distance between the phantom and the acoustic transducer. This distance was 40.9 cm. Then we used the acoustic transducer only as a receiver and synchronized the data acquisition to the laser pulse, which was repeated at a rate of 10 Hz. When the laser beam hit the black painted spot a strong photoacoustic signal was observed with an arrival time commensurate with the measured distance between the target and the acoustic transducer. When the laser beam was aimed off the black spot no photoacoustic signal was observed.

Next we repeated this experiment on one of the inventor's fingers as the imaging target. The finger was moved in front of the laser beam at a steady rate, thereby scanning the finger starting from the tip up to the mid section in 4 seconds at a speed of approximately 1 cm/s. At each laser pulse (every 0.1 seconds) the photoacoustic signal was recorded. In this experiment a 1064-nm laser illumination with 4-mJ energy per pulse was used. A total of 40 records (RF A-scans) were collected. To correct for any pulse-to-pulse variability, the laser intensity was also recorded using a photodiode that monitors a small fraction of the light coming out of the laser. To create a line scan the envelopes of the received photoacoustic signals were first detected and then normalized to the laser intensity for each pulse and then plotted as a function of distance. The resulting photoacoustic line scan clearly shows different features on the finger such as the nail, skin, and wrinkles in the skin.

Further proof of concept experiments have also been performed. In one experiment, PA imaging of a set of gray rectangles was performed. The rectangles had gray levels of 25%, 50%, 75%, 90% and 100%, dimensions of 0.12 inch by 0.13 inch, and were equally spaced by 0.12 inch. The laser parameters were: wavelength 532 nm, average pulse energy 94.7 µJ, and spot size 0.76 mm. The resulting image signal to noise ratio (SNR) was 31.7 dB. Visually, all of the rectangles except the 25% gray level were clearly resolved.

Similar experiments have resolved a set of black, red, green and blue squares, with SNRs of 25.2, 23.4, 16.2, and 17.1, respectively.

The invention claimed is:

1. Apparatus for photoacoustic (PA) superficial medical imaging, the apparatus comprising:
   a source of electromagnetic (EM) radiation configured to provide a beam of EM radiation to a superficial region of a patient, wherein the superficial region has an exposed surface, and wherein the beam of EM radiation provides a beam spot to the exposed surface;
   at least one acoustic receiver configured to receive acoustic radiation from the beam spot on the exposed surface;
   wherein the at least one acoustic receiver and the exposed surface are separated from each other by a gaseous medium;
   wherein the at least one acoustic receiver is substantially responsive to surface PA radiation generated by EM absorption at the exposed surface; and
   wherein the at least one acoustic receiver is substantially less responsive to bulk PA radiation generated by EM absorption at locations in the patient below the exposed surface than to the surface PA radiation.

2. The apparatus of claim 1, further comprising:
   a scanner configured to scan the beam of EM radiation over the exposed surface; and
   a processor configured to provide an image of photoacoustic signal versus location of the beam spot on the exposed surface.

3. The apparatus of claim 1, wherein the at least one acoustic receiver comprises an array of acoustic receiver elements.

4. An endoscope comprising the apparatus of claim 1.

5. Apparatus for screening skin comprising the apparatus of claim 1.

6. The apparatus of claim 1, wherein the at least one acoustic receiver is configured to distinguish the surface PA radiation from the bulk PA radiation by time of arrival at the at least one acoustic receiver.

7. The apparatus of claim 1, wherein the at least one acoustic receiver is configured to distinguish the surface PA radiation from the bulk PA radiation by relative amplitude of the surface PA radiation and the bulk PA radiation at the at least one acoustic receiver.

* * * * *